United States Patent [19]

Cherpeck

[11] Patent Number: 5,637,120
[45] Date of Patent: Jun. 10, 1997

[54] POLYOXYALKYLENE POLYLACTONE AMINOCARBAMATES AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 667,909

[22] Filed: Jun. 20, 1996

Related U.S. Application Data

[60] Provisional application No. 60/000,933 Jul. 6, 1995.

[51] Int. Cl.[6] .......................... C10L 1/22; C07C 269/00
[52] U.S. Cl. ............................. 44/387; 560/159
[58] Field of Search ........................ 44/387; 560/159

[56] References Cited

U.S. PATENT DOCUMENTS

| | | | |
|---|---|---|---|
| 4,160,648 | 7/1979 | Lewis et al. | 44/387 |
| 4,191,537 | 3/1980 | Lewis et al. | 44/71 |
| 4,197,409 | 4/1980 | Lilburn | 44/387 |
| 4,568,358 | 2/1986 | Courtney | 44/387 |
| 4,820,432 | 4/1989 | Lundberg et al. | 252/51.5 A |
| 4,881,945 | 11/1989 | Buckley, III | 44/387 |
| 4,933,485 | 6/1990 | Buckley, III | 44/387 |
| 5,028,667 | 7/1991 | McLain et al. | 525/415 |
| 5,306,314 | 4/1994 | Cherpeck | 44/387 |
| 5,312,460 | 5/1994 | Buckley, III | 44/387 |
| 5,322,529 | 6/1994 | Buckley, III | 44/387 |
| 5,366,517 | 11/1994 | Cherpeck | 44/387 |

OTHER PUBLICATIONS

P. Dubois et al., "Macromolecular Engineering of Polylactones and Polylactides. 8. Ring-Opening Polymerization of ε-Caprolactone Initiated by Primary Amines and Trialkylaluminum", *Macromolecules*, 1992, Month Unknown vol. 25, pp.2614–2618.

D. Tian et al., "Macromolecular Engineering of Polylactones and Polylactides. 18. Synthesis of Star–Branched Aliphatic Polyesters Bearing Various Functional End Groups", *Macromolecules*, 1994, Month Unknown vol. 27, pp. 4134–4144.

*Primary Examiner*—Margaret Medley
*Attorney, Agent, or Firm*—Claude J. Caroli

[57] ABSTRACT

Polyoxyalkylene polylactone aminocarbamates having the formula:

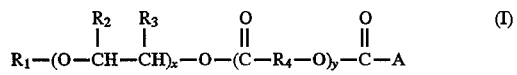

wherein
$R_1$ is a hydrocarbyl group having a sufficient number of carbon atoms to render the compound soluble in hydrocarbons boiling in the gasoline or diesel fuel range;

$R_2$ and $R_3$ are each independently hydrogen or lower alkyl having about 1 to about 6 carbon atoms and each $R_2$ and $R_3$ is independently selected in each —O—$CHR_2$—$CHR_3$— unit;

$R_4$ is an alkylene group of about 2 to about 5 carbon atoms;

A is a polyamine moiety having at least one basic nitrogen atom;

x is an integer from about 1 to about 100; and y is an integer from about 1 to about 25.

The polyoxyalkylene polylactone aminocarbamates of formula I are useful as fuel additives for the prevention and control of engine deposits.

48 Claims, No Drawings

POLYOXYALKYLENE POLYLACTONE AMINOCARBAMATES AND FUEL COMPOSITIONS CONTAINING THE SAME

CROSS-REFERENCE TO RELATED APPLICATIONS

This application claims priority from U.S. Provisional application Ser. No. 60/000,933, filed Jul. 6, 1995.

BACKGROUND OF THE INVENTION

1. Field of the Invention

This invention relates to novel end-functionalized polylactones. More particularly, this invention relates to novel polyoxyalkylene polylactone aminocarbamates and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, polyether amine fuel additives are well known in the art for the prevention and control of engine deposits. These polyether additives have a polyoxyalkylene "backbone", i.e., the polyether portion of the molecule consists of repeating oxyalkylene units. U.S. Pat. No. 4,191,537, issued Mar. 4, 1980 to R. A. Lewis et al., for example, discloses a fuel composition comprising a major portion of hydrocarbons boiling in the gasoline range and from 30 to 2,000 ppm of a hydrocarbyl polyoxyalkylene aminocarbamate having a molecular weight from about 600 to 10,000, and at least one basic nitrogen atom. The hydrocarbyl polyoxyalkylene moiety is composed of oxyalkylene units having from 2 to 5 carbon atoms in each oxyalkylene unit. These fuel compositions are taught to maintain the cleanliness of intake systems without contributing to combustion chamber deposits.

Poly(vinyl ether) amine fuel additives are also known in the art. For example, U.S. Pat. No. 5,306,314 discloses poly(vinyl ether) aminocarbamate fuel additives having a vinyl ether polymer backbone consisting of repeating vinyl ether units. These compounds are taught to be useful in fuel compositions to prevent and control engine deposits.

Polylactone polymer compositions have also been reported in the art. For example, U.S. Pat. No. 5,028,667 to McLain et al., discloses a process for the ring-opening polymerization of lactones using as catalyst compounds of yttrium and the rare earth metals. This patent further teaches that the resulting polylactone polymers are useful as biodegradable polymers for medical uses and as flexible films for packaging.

P. Dubois et al., in *Macromolecules,* 1992, Volume 25, pp. 2,614–2,618, describe the ring-opening polymerization of ε-caprolactone initiated by primary amines and trialkylaluminum. The resulting polycaprolactone is taught to be useful in the biomedical field due to its high permeability, lack of toxicity for living organisms, biodegradability, and capacity to be blended with various commercial polymers over a wide composition range.

D. Tian et al., in *Macromolecules,* 1994, Volume 27, pp. 4,134–4,144, describe star-branched polycaprolactone polymers having primary amine end groups. These polymers are prepared by the ring-opening polymerization of ε-caprolactone with aluminum alkoxides and a trimesic acid trichloride termination agent.

U.S. Pat. No. 4,820,432 to Lundberg et al. discloses poly ($C_5$ to $C_9$ lactone) modified Mannich base adducts which are prepared by reacting a $C_5$ to $C_9$ lactone, an amine, an aldehyde, an N-hydroxyarylamine, and a hydrocarbyl substituted $C_4$ to $C_{10}$ monounsaturated dicarboxylic acid producing material, such as a polyisobutenyl succinic anhydride. These modified Mannich base adducts may be prepared, for example, by first reacting an N-hydroxyarylamine with a hydrocarbyl substituted dicarboxylic acid producing material to form an N-hydroxyaryl hydrocarbyl substituted imide, which is subsequently reacted with an aldehyde and an amine to form an intermediate Mannich base adduct having an amino functional group capable of initiating lactone ring opening polymerization, and then reacting the intermediate Mannich base adduct with a $C_5$ to $C_9$ lactone. This patent further teaches that the resulting poly ($C_5$ to $C_9$ lactone) modified Mannich base adduct is useful as an oil soluble dispersant additive for fuel and lubricating oil compositions.

It has now been discovered that certain polyoxyalkylene polylactone aminocarbamates provide excellent control of engine deposits, especially intake valve deposits, when employed as fuel additives in fuel compositions.

SUMMARY OF THE INVENTION

The present invention provides novel fuel-soluble polyoxyalkylene polylactone aminocarbamate fuel additives which are useful for the prevention and control of engine deposits, particularly intake valve deposits.

The fuel-soluble polyoxyalkylene polylactone aminocarbamates of the present invention have the formula:

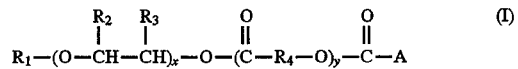

wherein

R$_1$ is a hydrocarbyl group having a sufficient number of carbon atoms to render the compound soluble in hydrocarbons boiling in the gasoline or diesel fuel range;

R$_2$ and R$_3$ are each independently hydrogen or lower alkyl having about 1 to about 6 carbon atoms and each R$_2$ and R$_3$ is independently selected in each —O—CHR$_2$—CHR$_3$— unit;

R$_4$ is an alkylene group of about 2 to about 5 carbon atoms;

A is a polyamine moiety having at least one basic nitrogen atom;

x is an integer from about 1 to about 100; and y is an integer from about 1 to about 25.

The present invention further provides a fuel composition comprising a major amount of hydrocarbons boiling in the gasoline or diesel range and an effective deposit-controlling amount of a polyoxyalkylene polylactone aminocarbamate of the present invention.

The present invention additionally provides a fuel concentrate comprising an inert stable oleophilic organic solvent boiling in the range of from about 150° F. to about 400°

F. (about 65° C. to about 205° C.) and from about 10 to about 70 weight percent of a polyoxyalkylene polylactone aminocarbamate of the present invention.

Among other factors, the present invention is based on the surprising discovery that certain polyoxyalkylene polylactone aminocarbamates provide excellent control of engine deposits, especially on intake valves, when employed as fuel additives in fuel compositions.

DETAILED DESCRIPTION OF THE INVENTION

The fuel additives provided by the present invention have the general formula:

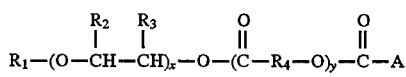

wherein A, $R_1$, $R_2$, $R_3$, $R_4$, x, and y are as defined above.

A is preferably a polyamine moiety containing about 2 to about 12 amine nitrogen atoms and from about 2 to about 40 carbon atoms. More preferably, A is a polyamine moiety derived from a polyalkylene polyamine containing about 2 to about 12 nitrogen atoms and about 2 to about 24 carbon atoms. Still more preferably, A is a polyamine moiety derived from a polyalkylene polyamine having the formula:

wherein $R_5$ is an alkylene group having about 2 to about 6 carbon atoms and z is an integer from about 1 to about 4. Most preferably, A is a polyamine moiety derived from ethylene diamine or diethylene triamine.

Preferably, $R_1$ is a hydrocarbyl group having from about 1 to about 120 carbon atoms. More preferably, $R_1$ is alkyl having about 1 to about 100 carbon atoms or alkylphenyl having an alkyl group containing about 1 to about 100 carbon atoms. Still more preferably, $R_1$ is alkyl having about 1 to about 30 carbon atoms or alkylphenyl having an alkyl group containing about 1 to about 30 carbon atoms. Even more preferably, $R_1$ is alkyl having about 2 to about 24 carbon atoms or alkylphenyl having an alkyl group containing about 2 to about 24 carbon atoms. Most preferably, $R_1$ is alkyl having about 4 to about 12 carbon atoms or alkylphenyl having an alkyl group containing about 4 to about 12 carbon atoms.

Preferably, at least one of $R_2$ and $R_3$ is hydrogen.

$R_4$ is preferably an alkylene group having about 4 to about 5 carbon atoms. More preferably, $R_4$ is an alkylene group having about 5 carbon atoms.

Preferably, x is an integer from about 1 to about 30. More preferably, x is about 1 to about 10.

Preferably, y is an integer from about 1 to about 10. More preferably, y is an integer from about 1 to about 5.

A preferred group of polyoxyalkylene polylactone aminocarbamates are those of formula I wherein A is derived from a polyalkylene polyamine containing about 2 to about 12 nitrogen atoms and about 2 to about 24 carbon atoms; $R_1$ is alkyl having about 1 to about 100 carbon atoms or alkylphenyl having an alkyl group containing about 1 to about 100 carbon atoms; at least one of $R_2$ and $R_3$ is hydrogen; $R_4$ is alkylene having about 4 to about 5 carbon atoms; x is an integer from about 1 to about 30; and y is an integer from about 1 to about 10.

The polyoxyalkylene polylactone aminocarbamates of the present invention will generally have a sufficient molecular weight so as to be non-volatile at normal engine intake valve operating temperatures. Typically, the molecular weight of the polyoxyalkylene polylactone aminocarbamates of this invention will range from about 250 to about 5,000, preferably from about 250 to about 3,000.

DEFINITIONS

As used herein the following terms have the following meanings unless expressly stated to the contrary.

The term "hydrocarbyl" refers to an organic radical primarily composed of carbon and hydrogen which may be aliphatic, alicyclic, aromatic or combinations thereof, e.g., aralkyl or alkaryl. Such hydrocarbyl groups are generally free of aliphatic unsaturation, i.e., olefinic or acetylenic unsaturation, but may contain minor amounts of heteroatoms, such as oxygen or nitrogen, or halogens, such as chlorine.

The term "alkyl" refers to both straight- and branched-chain alkyl groups.

The term "alkylene" refers to straight- and branched-chain alkylene groups having at least 2 carbon atoms. Typical alkylene groups include, for example, ethylene ($—CH_2CH_2—$), propylene ($—CH_2CH_2CH_2—$), isopropylene ($—CH(CH_3)CH_2—$), n-butylene ($—CH_2CH_2CH_2CH_2—$), sec-butylene ($—CH(CH_2CH_3)CH_2—$), n-pentylene ($—CH_2CH_2CH_2CH_2CH_2—$), and the like.

The term "polyoxyalkylene" refers to a polymer or oligomer having the general formula:

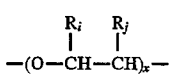

wherein $R_i$ and $R_j$ are each independently hydrogen or lower alkyl groups, and x is an integer from about 1 to about 100. When referring herein to the number of oxyalkylene units in a particular polyoxyalkylene compound, it is to be understood that this number refers to the average number of oxyalkylene units in such compounds unless expressly stated to the contrary. For purposes of the present invention, the term "polyoxyalkylene" is meant to include those compounds having only about 1 oxyalkylene unit, that is, those compounds wherein x is 1.

The term "polylactone" refers to a ring-opened lactone polymer having the general formula:

wherein $R_4$ is an alkylene group of about 2 to about 5 carbon atoms and y is an integer from about 1 to about 25. The term "lactone unit" refers to one monomeric unit of a polylactone polymer. Such polylactone polymers are obtained by the ring-opening polymerization of a lactone. When referring herein to the number of lactone units in a polylactone compound, it is to be understood that this number refers to the average number of lactone units in such compounds unless expressly stated to the contrary.

Also, for purposes of the present invention, the term "polylactone" is meant to include those ring-opened compounds having only about 1 lactone unit, that is, those compounds wherein y is about 1.

GENERAL SYNTHETIC PROCEDURES

The polyoxyalkylene polylactone aminocarbamates of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The polyoxyalkylene polylactone aminocarbamates of the present invention contain (a) a polylactone component, (b) an amine component, and (c) a carbamate connecting group which covalently links the polylactone component and the amine component.

A. The Polylactone Component

The polylactone component of the polyoxyalkylene polylactone aminocarbamates of the present invention is a polyoxyalkylene-substituted lactone polymer containing about 1 to about 25 lactone units. Generally, the polylactone component will have a polyoxyalkylene-substituted lactone unit at one end of the lactone polymer and will be terminated with a hydroxyl group at the other end of the lactone polymer.

The polylactone component of the polylactone aminocarbamates of this invention is preferably prepared by polymerizing certain lactone monomers under "living polymerization" conditions. The term "living polymerization" is well known in the art and refers to polymerization reactions which occur in the substantial absence of chain transfer and termination reactions. Under such conditions, the reactive end of the growing polymer is essentially stable indefinitely. Accordingly, each lactone monomer can be added sequentially to the growing polylactone chain in a controlled step-by-step manner. Thus, living polymerization allows polylactones to be prepared having a substantially predictable sequence of lactone units.

In general, the polylactone polymer may be prepared by first reacting a polyoxyalkylene alcohol of the formula:

(III)

Wherein $R_1$, $R_2$, $R_3$, and x are as defined above, with a suitable lactone polymerization catalyst, such as trialkylaluminum, to form a polymerization initiator which is subsequently reacted with a lactone of the formula:

(IV)

wherein $R_4$ is as defined above, to provide the desired polylactone having the formula:

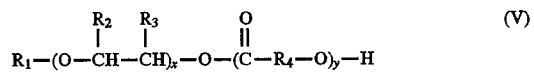

(V)

wherein $R_1$, $R_2$, $R_3$, $R_4$, x, and y are as defined above.

For example, when employing trimethylaluminum as the polymerization catalyst, the reaction sequence may be described as follows:

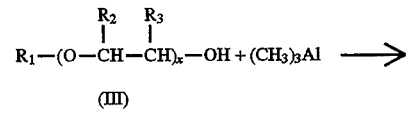

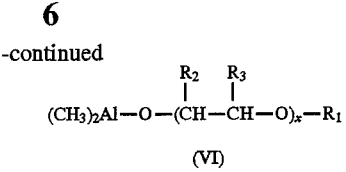

(VI)

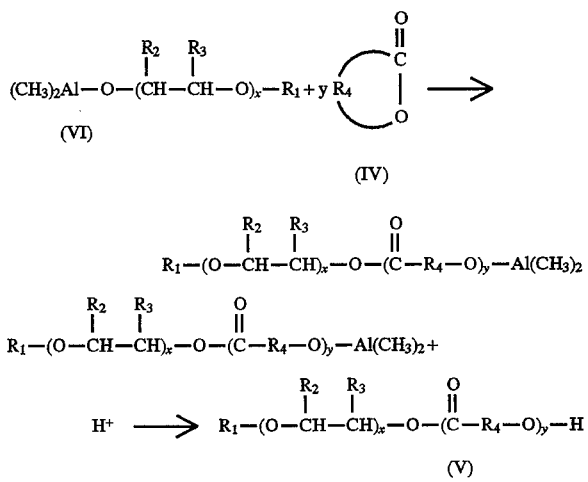

The polyoxyalkylene alcohols of formula III are known compounds that can be prepared using conventional procedures. For example, suitable procedures for preparing such compounds are taught in U.S. Pat. Nos. 2,782,240 and 2,841,479, the disclosures of which are incorporated herein by reference.

Preferably, the polyoxyalkylene alcohols of formula III are prepared by contacting an alkoxide or phenoxide metal salt having the formula:

$$R_6\text{—O—M} \qquad \text{(VII)}$$

wherein $R_6$ is an alkyl, phenyl, aralkyl, or alkaryl group and M is a metal cation, such as lithium, sodium, potassium, and the like, with about 1 to about 100 molar equivalents of an alkylene oxide (an epoxide) having the formula:

(VIII)

wherein $R_2$ and $R_3$ are as defined above.

Typically, metal salt VII is prepared by contacting the corresponding hydroxy compound $R_6OH$ with a strong base, such as sodium hydride, potassium hydride, sodium amide, and the like, in an inert solvent, such as toluene, xylene, and the like, under substantially anhydrous conditions at a temperature in the range from about −10° C. to about 120° C. for about 0.25 to about 3.0 hours.

Metal salt VII is generally not isolated, but is reacted in situ with alkylene oxide VIII to provide, after neutralization, the polyoxyalkylene alcohol III. This polymerization reaction is typically conducted in a substantially anhydrous inert solvent at a temperature of about 30° C. to about 150° C. for about 2.0 to about 120 hours. Suitable solvents for this reaction, include toluene, xylene, and the like. Typically, the reaction is conducted at a pressure sufficient to contain the reactants and the solvent, preferably at atmospheric or ambient pressure.

The amount of alkylene oxide employed in this reaction will generally depend on the number of oxyalkylene units desired in the product. Typically, the molar ratio of alkylene oxide VIII to metal salt VII will range from about 1:1 to about 100:1; preferably, from about 1:1 to about 30:1, more preferably from about 1:1 to about 10:1.

Alkylene oxides suitable for use in this polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides; and the like. Preferred alkylene oxides are propylene oxide, 1,2-butylene oxide, and ethylene oxide.

In the polymerization reaction, a single type of alkylene oxide may be employed, e.g., propylene oxide, in which case the product is a homopolymer, e.g., a poly(oxypropylene) polymer. Copolymers are equally satisfactory and random copolymers can be prepared by contacting metal salt VII with a mixture of alkylene oxides, such as a mixture of propylene oxide and 1,2-butylene oxide, under polymerization conditions. Copolymers containing blocks of oxyalkylene units are also suitable for use in this invention. Block copolymers can be prepared by contacting metal salt VII with first one alkylene oxide, then others in any order, or repetitively, under polymerization conditions.

The polyoxyalkylene alcohol III may also be prepared by living or immortal polymerization as described by S. Inoue and T. Aida in *Encyclopedia of Polymer Science and Engineering*, Second Edition, Supplemental Volume, J. Wiley and Sons, New York, pp. 412–420 (1989). These procedures are especially useful for preparing polyoxyalkylene alcohols of formula III in which $R_2$ and $R_3$ are both alkyl groups.

As noted above, the alkoxide or phenoxide metal salt used in the above procedures is generally derived from the corresponding hydroxy compound, $R_6OH$. Suitable hydroxy compounds include straight- or branched-chain aliphatic alcohols having about 1 to about 100 carbon atoms and phenols having the formula:

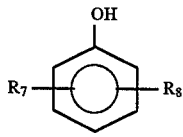

(IX)

wherein $R_7$ is an alkyl group having about 1 to about 100 carbon atoms and $R_8$ is hydrogen; or $R_7$ and $R_8$ are both alkyl groups, each independently containing about 1 to about 50 carbon atoms.

Representative examples of straight- or branched-chain aliphatic alcohols suitable for use in this invention include, but are not limited to, n-butanol; isobutanol; sec-butanol; t-butanol; n-pentanol; n-hexanol; n-heptanol; n-octanol; isooctanol; n-nonanol; n-decanol; n-dodecanol; n-hexadecanol (cetyl alcohol); n-octanol (stearyl alcohol); alcohols derived from linear $C_{10}$ to $C_{30}$ alpha olefins and mixtures thereof; and alcohols derived from polymers of $C_2$ to $C_6$ olefins, such as alcohols derived from polypropylene and polybutene, including polypropylene alcohols having about 9 to about 100 carbon atoms and polybutene alcohols having about 12 to about 100 carbon atoms. Preferred straight- or branched-chain aliphatic alcohols will contain about 1 to about 30 carbon atoms, more preferably about 2 to about 24 carbon atoms, and most preferably about 4 to about 12 carbon atoms.

The phenols of formula IX may be monoalkyl-substituted phenols or dialkyl-substituted phenols. Monoalkyl-substituted phenols are preferred, especially monoalkylphenols having an alkyl substituent in the para position.

Preferably, the alkyl group of the alkylphenol will contain about 1 to about 30 carbon atoms, more preferably about 2 to about 24 carbon atoms, and most preferably about 4 to about 12 carbon atoms. Representative examples of alkyl phenols suitable for use in this invention include, but are not limited to, methylphenol, dimethylphenol, ethylphenol, butylphenol, octylphenol, decylphenol, dodecylphenol, tetradecylphenol, hexadecylphenol, octaphenol, eicosylphenol, tetracosylphenol, hexacosylphenol, triacontylphenol, and the like. Also, mixtures of alkylphenols may be employed, such as a mixture of $C_{14}$ to $C_{18}$ alkylphenols, a mixture of $C_{18}$ to $C_{24}$ alkylphenols, a mixture of $C_{20}$ to $C_{24}$ alkylphenols, or a mixture of $C_{16}$ to $C_{26}$ alkylphenols.

Particularly preferred alkylphenols are prepared by alkylating phenol with polymers or oligomers of $C_3$ to $C_6$ olefins, such as polypropylene or polybutene. These polymers typically contain about 8 to about 100 carbon atoms, preferably about 10 to about 30 carbon atoms. An especially preferred alkylphenol is prepared by alkylating phenol with a propylene polymer having an average of about 4 units. This polymer has the common name of propylene tetramer and is commercially available.

As noted above, the polyoxyalkylene alcohol $R_1$—(O—$CHR_2$—$CHR_3$)$_x$—OH is reacted with a lactone polymerization catalyst to form a polymerization initiator. Suitable lactone polymerization catalysts include alkali and alkaline earth metal hydrides, alkoxides and alkyls; alkyl aluminum and alkyl zinc compounds; alkoxides of aluminum, titanium, zirconium and tin; yttrium and rare earth metal alkoxides; and the like.

Preferred polymerization catalysts for use with the polyoxyalkylene alcohol $R_1$—(O—$CHR_2$—$CHR_3$)$_x$—OH are the trialkylaluminums, such as trimethylaluminum and triethylaluminum.

Generally, the reaction of the polyoxyalkylene alcohol $R_1$—(O—$CHR_2$—$CHR_3$)$_x$—OH with the polymerization catalyst will be conducted in a substantially anhydrous inert solvent at a temperature of about −50° C. to about 150° C., preferably about −10° C. to about 50° C. Suitable inert solvents include benzene, toluene, dichloromethane, diethyl ether, and the like. Preferably, the reaction will be conducted under a dry inert gas atmosphere, such as nitrogen or argon, at about atmospheric or ambient pressure. Typically, the molar ratio of alcohol to polymerization catalyst will range from about 0.5:1 to about 5:1.

In the second stage of the polymerization process, the reaction product of the polyoxyalkylene alcohol $R_1$—(O—$CHR_2$—$CHR_3$)$_x$—OH and the polymerization catalyst, such as the polyoxyalkylene alcohol-catalyst adduct of formula VI, is reacted with a lactone monomer of formula IV. In this reaction the polyoxyalkylene alcohol-catalyst adduct functions as an initiator for the lactone polymerization.

Suitable lactone monomers for use in the present invention include simple lactones containing from about 3 to about 6 carbon atoms, such as β-propiolactone, α-methyl-β-propiolactone, β-methyl-β-propiolactone, β-butyrolactone, γ-butyrolactone, γ-valerolactone, δ-valerolactone, δ-caprolactone, ε-caprolactone, and the like. Preferred lactone monomers include δ-valerolactone and ε-caprolactone. An especially preferred lactone monomer is ε-caprolactone.

Typically, the living polymerization reaction will be conducted in a substantially anhydrous inert solvent which may be the same or different than the solvent employed in forming the polymerization initiator. The polymerization reaction temperature will generally be in the range of about −50° C. to about 150° C., preferably from about −10° C. to about 50° C. Generally, the polymerization reaction will be carried out under a dry, inert gas atmosphere, such as nitrogen or argon, at about atmospheric or ambient pressure.

The molar ratio of lactone monomer to the polymerization initiator, such as the adduct of formula VI, will generally range from about 1:1 to about 25:1, preferably from about 1:1 to about 10:1, and more preferably from about 1:1 to about 5:1.

The time employed for the polymerization reaction can vary over a wide range and will depend to some extent on the reaction temperature and on the lactone monomers used in the polymerization process. Generally, the reaction will be conducted for about 0.05 to about 20 hours, preferably about 0.05 to about 2.0 hours or until essentially all the lactone monomers have reacted to form polymer.

When essentially all of the lactone monomer has reacted to form polymer, the reactive terminal end of the polymer is quenched by contacting the reaction mixture with about 1 to about 100 equivalents of an aqueous acid solution, such as aqueous hydrochloric acid. This affords a hydroxy-terminated polylactone of formula V.

The living polymerization of lactones is well known in the art and is further described, for example, in P. Dubois et al., *Macromolecules*, 1992, Volume 25, pp. 2,614–2,618; D. Tian et al., *Macromolecules*, 1994, Volume 27, pp. 4,134–4,144; and K. J. Ivin and T. Saegusa, *Ring-Opening Polymerization*, Volume 1, Chapter 7, Elsevier, London, 1984, and references cited therein.

The hydroxy-terminated polylactone of formula V may then be coupled with a suitable amine component using phosgene or a phosgene equivalent as described in further detail below.

B. The Amine Component

As indicated above, the polyoxyalkylene polylactone aminocarbamates of the present invention contain an amine component which is covalently linked to the aforementioned polylactone component through a carbamate connecting group.

In general, the amine component will contain an average of at least about one basic nitrogen atom per molecule. A "basic nitrogen atom" is one that is titratable by a strong acid, for example, a primary, secondary, or tertiary amine nitrogen; as distinguished from, for example, an carbamyl nitrogen, e.g., —OC(O)NH—, which is not titratable with a strong acid. Preferably, at least one of the basic nitrogen atoms of the amine component will be primary or secondary amine nitrogen, more preferably at least one will be a primary amine nitrogen.

The amine component of the polyoxyalkylene polylactone aminocarbamates of this invention is preferably derived from a polyamine containing about 2 to about 12 amine nitrogen atoms and from about 2 to about 40 carbon atoms. Polyamines having a carbon-to-nitrogen ratio of from about 1:1 to about 10:1 are particularly preferred.

In preparing the compounds of this invention using a polyamine where the various nitrogen atoms of the polyamine are not geometrically equivalent, several substitutional isomers are possible and each of these possible isomers is encompassed within this invention.

Suitable polyamines can have a straight- or branched-chain structure and may be cyclic or acyclic or combinations thereof. Generally, the amine nitrogen atoms of such polyamines will be separated from one another by at least two carbon atoms, i.e., polyamines having an aminal structure are not suitable. The polyamine may also contain one or more oxygen atoms, typically present as an ether or a hydroxyl group.

A particularly preferred group of polyamines for use in the present invention are polyalkylene polyamines, including alkylene diamines. Such polyalkylene polyamines will typically contain about 2 to about 12 nitrogen atoms and about 2 to about 24 carbon atoms. Preferably, the alkylene groups of such polyalkylene polyamines will contain from about 2 to about 6 carbon atoms, more preferably from about 2 to about 4 carbon atoms.

Examples of suitable polyalkylene polyamines include ethylenediamine, propylenediamine, isopropylenediamine, butylenediamine, pentylenediamine, hexylenediamine, diethylenetriamine, dipropylenetriamine, dimethylaminopropylamine, diisopropylenetriamine, dibutylenetriamine, di-sec-butylenetriamine, triethylenetetraamine, tripropylenetetraamine, triisobutylenetetraamine, tetraethylenepentamine, pentaethylenehexamine, dimethylaminopropylamine, and mixtures thereof.

Particularly suitable polyalkylene polyamines are those having the formula:

$$H_2N—(R_5NH)_z—H \qquad (X)$$

wherein $R_3$ is a straight- or branched-chain alkylene group having about 2 to about 6 carbon atoms, preferably about 2 to about 4 carbon atoms, most preferably about 2 carbon atoms, i.e., ethylene (—$CH_2CH_2$—); and z is an integer from about 1 to about 4, preferably about 1 or about 2.

Particularly preferred polyalkylene polyamines are ethylenediamine, diethylenetriamine, triethylenetetraamine, and tetraethylenepentamine. Most preferred are ethylenediamine and diethylenetriamine, especially ethylenediamine.

Also contemplated for use in the present invention are cyclic polyamines having one or more 5- to 6-membered rings. Such cyclic polyamines compounds include piperazine, 2-methylpiperazine, N-(2-aminoethyl) piperazine, N-(2-hydroxyethyl)piperazine, 1,2-bis-(N-piperazinyl)ethane, 3-aminopyrrolidine, N-(2-aminoethyl) pyrrolidine, and the like. Among the cyclic polyamines, the piperazines are preferred.

Many of the polyamines suitable for use in the present invention are commercially available and others may be prepared by methods which are well known in the art. For example, methods for preparing amines and their reactions are detailed in Sidgewick's "*The Organic Chemistry of Nitrogen*", Clarendon Press, Oxford, 1966; Noller's "*Chemistry of Organic Compounds*", Saunders, Philadelphia, 2nd Ed., 1957; and Kirk-Othmer's "*Encyclopedia of Chemical Technology*", 2nd Ed., especially Volume 2, pp. 99–116.

C. The Carbamate Connecting Group

The carbamate connecting group which covalently links the polylactone component to the amine component has the formula:

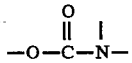

wherein the ether oxygen may be regarded as being derived from the hydroxyl group of a hydroxy-terminated polylactone of formula V; and the nitrogen atom may be regarded as being derived from a nitrogen atom of a suitable amine component. The carbonyl group, —C(O)—, is preferably provided by a carbonyl-containing coupling agent, such as phosgene or a phosgene equivalent. Suitable phosgene equivalents include, for example, 1,1'-carbonyldiimidazole, trichloromethyl chloroformate (diphosgene), and bis (trichloromethyl) carbonate (triphosgene).

The polyoxyalkylene polylactone aminocarbamates of the present invention are preferably prepared, for example, by contacting a hydroxy-terminated polylactone of formula V with 1,1'-carbonyldiimidazole to produce a polylactone acylimidazole. The acylimidazole is then contacted with a suitable polyamine to afford a polyoxyalkylene polylactone aminocarbamate.

The reaction of the hydroxy-terminated polylactone of formula V with 1,1'-carbonyldiimidazole is typically conducted on an essentially equimolar basis, although excess 1,1'-carbonyldiimidazole can be used to increase the yield of the acylimidazole. The reaction may be conducted by contacting the hydroxy-terminated polylactone with 1,1'-carbonyldiimidazole at temperatures ranging from about −10° C. to about 200° C., typically in an inert solvent, such as benzene, toluene, dichloromethane, and the like, for about 0.25 to about 5.0 hours.

A polyoxyalkylene polylactone aminocarbamate is then formed by contacting the polylactone acylimidazole with a suitable polyamine at a temperature ranging from about 0° C. to about 150° C. for about 1.0 to about 24 hours. This reaction may be conducted with or without an inert solvent. Suitable inert solvents include benzene, toluene, dichloromethane, and the like. The molar ratio of polyamine to polylactone acylimidazole will generally range from about 2:1 to about 20:1, preferably about 5:1 to about 10:1. The desired product may be obtained by washing the reaction mixture with water and stripping the mixture, usually under vacuum, to remove any residual solvent.

Fuel Compositions

The polyalkylene polylactone aminocarbamates of the present invention are useful as additives in hydrocarbon fuels to prevent and control engine deposits, particularly intake valve deposits. Typically, the desired deposit control will be achieved by operating an internal combustion engine with a fuel composition containing a polyoxyalkylene polylactone aminocarbamate of the present invention. The proper concentration of additive necessary to achieve the desired deposit control varies depending upon the type of fuel employed, the type of engine, and the presence of other fuel additives.

In general, the concentration of the polyoxyalkylene polylactone aminocarbamates of this invention in hydrocarbon fuel will range from about 50 to about 2,500 parts per million (ppm) by weight, preferably from about 75 to about 1,000 ppm. When other deposit control additives are present, a lesser amount of the present additive may be used. Furthermore, lower concentrations of, for example, about 30 to about 70 ppm may be preferred when the present additives are employed as carburetor detergents only.

The polyoxyalkylene polylactone aminocarbamates of the present invention may be formulated as a concentrate using an inert stable oleophilic (i.e., dissolved in gasoline) organic solvent boiling in the range of about 150° F. to about 400° F. (about 65° C. to about 205° C.). Preferably, an aliphatic or an aromatic hydrocarbon solvent is used, such as benzene, toluene, xylene, or higher-boiling aromatics or aromatic thinners. Aliphatic alcohols containing about 3 to about 8 carbon atoms, such as isopropanol, isobutylcarbinol, n-butanol, and the like, in combination with hydrocarbon solvents are also suitable for use with the present additives. In the concentrate, the amount of the additive will generally range from about 10 to about 70 weight percent, preferably about 10 to about 50 weight percent, more preferably from about 10 to about 25 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators, and demulsifiers may be present.

In diesel fuels, other well-known additives can be employed, such as pour point depressants, flow improvers, cetane improvers, and the like.

A fuel-soluble, nonvolatile carrier fluid or oil may also be used with the polyalkylene polylactone aminocarbamates of this invention. The carrier fluid is a chemically inert hydrocarbon-soluble liquid vehicle which substantially increases the nonvolatile residue (NVR) or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis and polyesters, such as those described, for example, in U.S. Pat. Nos. 3,756,793 and 5,004,478, and in European Patent Application Nos. 356,726 and 382,159.

These carrier fluids are believed to act as a carrier for the fuel additives of the present invention and to assist in removing and retarding deposits. The carrier fluid may also exhibit synergistic deposit control properties when used in combination with the polyoxyalklylene polylactone aminocarbamates of this invention.

The carrier fluids are typically employed in amounts ranging from about 100 to about 5,000 ppm by weight of the hydrocarbon fuel, preferably from about 400 to about 3,000 ppm of the fuel. Preferably, the ratio of carrier fluid to deposit control additive will range from about 0.5:1 to about 10:1, more preferably from about 2:1 to about 5:1, most preferably about 4:1.

When employed in a fuel concentrate, carrier fluids will generally be present in amounts ranging from about 20 to about 60 weight percent, preferably from about 30 to about 50 weight percent.

EXAMPLES

The following examples are presented to illustrate specific embodiments of the present invention and synthetic preparations thereof and should not be interpreted as limitations upon the scope of the invention.

EXAMPLE 1

Preparation of

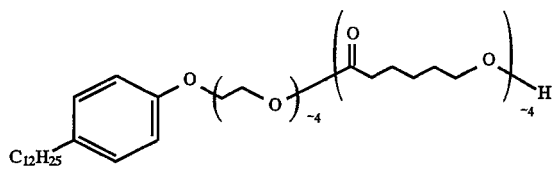

Trimethylaluminum (25.3 mL of a 2.0M solution in toluene) was added to anhydrous dichloromethane (100 mL) via syringe under nitrogen. The solution was cooled to 0° C. and dodoxynol-4 (commercially available from Huntsman Chemical Corporation as Rexol 65/4, 22.0 grams dissolved in 100 mL of anhydrous dichloromethane) was added dropwise. The reaction was stirred at room temperature for 30 minutes and then cooled back to 0° C. ε-Caprolactone (22.2 mL) was added all at once, the cooling bath was removed and the reaction was stirred at room temperature for sixteen hours. The reaction was quenched with 100 mL of 5% aqueous hydrochloric acid and was extracted three times with dichloromethane. The combined organic layers were dried over anhydrous magnesium sulfate, filtered and the solvents removed in vacuo to yield 50.2 grams of the desired product.

EXAMPLE 2

Preparation of

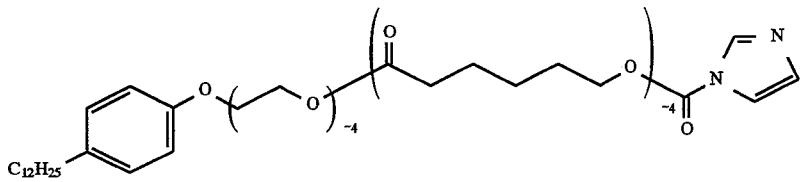

1,1'-Carbonyldiimidazole (6.1 grams) was added to the product from Example 1 (13.0 grams) dissolved in dichloromethane (200 mL). The reaction was stirred under nitrogen at room temperature for 4 hours and then diluted with dichloromethane (600 mL). Water (400 mL) was added and the mixture was stirred for ten minutes at room temperature. The phases were separated, and the organic phase was washed with water twice more, dried over anhydrous sodium sulfate, filtered and the solvents removed in vacuo to yield 17.0 grams of the desired product.

EXAMPLE 3

Preparation of

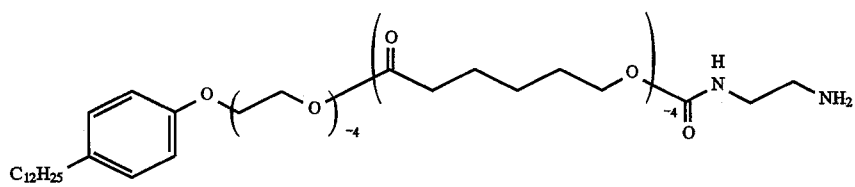

The product from Example 2 (17.0 grams) dissolved in anhydrous dichloromethane (100 mL) was added dropwise to ethylenediamine (11.4 mL) dissolved in anhydrous dichloromethane (100 mL) under nitrogen at room temperature. The reaction was stirred at room temperature for four hours, diluted with dichloromethane (600 mL), washed twice with water (300 mL), dried over anhydrous sodium sulfate, filtered and the solvents removed in vacuo to yield 13.0 grams of the desired product. $^1$H NMR (CDCl$_3$) δ 7.0–7.25 (m, 2H), 6.8–7.0 (m, 2H), 3.6–4.4 (m, 24H), 3.2 (m, 2H), 2.75 (t, 2H), 2.3 (t, 8H), 0.4–1.8 (m, 49H).

EXAMPLE 4

Preparation of

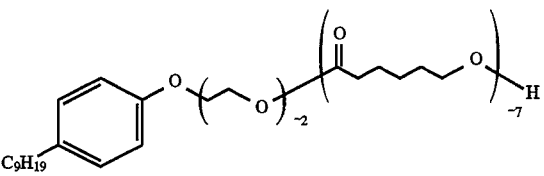

Trimethylaluminum (30.0 mL of a 2.0M solution in toluene) was added to anhydrous dichloromethane (100 mL) via syringe under nitrogen. Nonoxynol-2 was obtained by chromatographing Rexol 25/1 (commercially available from Huntsman Chemical Corporation) on silica gel eluting with hexane:diethyl ether (1:1). The solution was cooled to 0° C. and the nonoxynol-2 (18.0 grams dissolved in 100 mL of anhydrous dichloromethane) was added dropwise. The reaction was stirred at room temperature for 30 minutes and then cooled back to 0° C. ε-Caprolactone (59.8 mL) was added all at once, the cooling bath was removed and the reaction was stirred at room temperature for sixteen hours. The reaction was quenched with 100 mL of 5% aqueous hydrochloric acid and was extracted three times with dichloromethane. The combined organic layers were dried over anhydrous magnesium sulfate, filtered and the solvents removed in vacuo to yield 76.3 grams of the desired product.

EXAMPLE 5

Preparation of

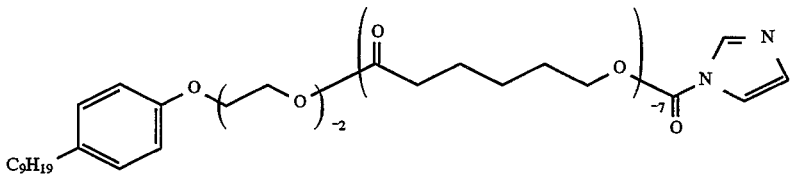

1,1'-Carbonyldiimidazole (9.7 grams) was added to the product from Example 4 (30.0 grams) dissolved in dichloromethane (500 mL). The reaction was stirred under nitrogen at room temperature for 4 hours and then diluted with dichloromethane (1 L). Water (300 mL) was added and the mixture was stirred for ten minutes at room temperature. The phases were separated, and the organic phase was washed with water twice more, dried over anhydrous sodium sulfate, filtered and the solvents removed in vacuo to yield 29.8 grams of the desired product.

EXAMPLE 6

Preparation of

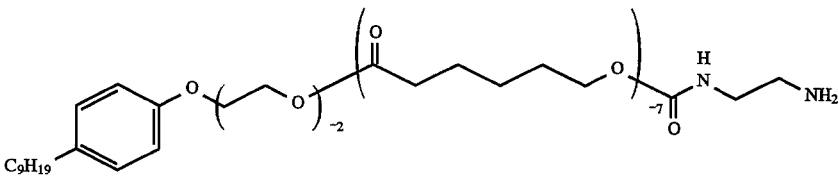

The product from Example 5 (20.0 grams) dissolved in anhydrous dichloromethane (100 mL) was added dropwise to ethylenediamine (10.3 mL) dissolved in anhydrous dichloromethane (100 mL) under nitrogen at room temperature. The reaction was stirred at room temperature for two hours, diluted with dichloromethane (600 mL), washed twice with water (300 mL), dried over anhydrous sodium sulfate, filtered and the solvents removed in vacuo to yield 14.1 grams of the desired product. $^1$H NMR (CDCl$_3$) $\delta$ 7.1–7.25 (m, 2H), 6.8–7.0 (m, 2H), 4.5 (t, 2H), 4.2 (t, 2H), 4.1 (t, 18H), 3.25 (t,2H), 2.75 (t, 2H), 2.3 (t, 14H), 0.4–1.8 (m, 61H).

EXAMPLE 7

Single-Cylinder Engine Test

The test compounds were blended in gasoline and their deposit reducing capacity determined in an ASTM/CFR single-cylinder engine test. A Waukesha CFR single-cylinder engine was used. Each run was carried out for 15 hours, at the end of which time the intake valve was removed, washed with hexane, and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1,800 rpm; the crankcase oil is a commercial 30W oil.

The amount of carbonaceous deposit in milligrams on the intake valves is reported for each of the test compounds in Table I.

TABLE I

| | Single-Cylinder Engine Test Results | | |
|---|---|---|---|
| | Intake Valve Deposit Weight (in milligrams) | | |
| Sample[1] | Run 1 | Run 2 | Average |
| Base Fuel | 300.1 | 302.3 | 301.2 |
| Example 3 | 13.1 | 16.3 | 14.7 |
| Example 6 | 40.2 | 20.5 | 30.4 |

[1]At 150 parts per million actives (ppma).

The base fuel employed in the above single-cylinder engine tests was a regular octane unleaded gasoline containing no fuel detergent. The test compounds were admixed with the base fuel to give a concentration of 150 ppma (parts per million actives).

The data in Table I illustrates the significant reduction in intake valve deposits provided by a polyoxyalkylene polylactone aminocarbamate of the present invention (Examples 3, 6) compared to the base fuel.

What is claimed is:

1. A fuel-soluble compound of the formula:

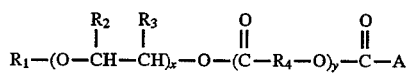

wherein $R_1$ is a hydrocarbyl group having a sufficient number of carbon atoms to render the compound soluble in hydrocarbons boiling in the gasoline or diesel fuel range;

$R_2$ and $R_3$ are each independently hydrogen or lower alkyl having about 1 to about 6 carbon atoms and each $R_2$ and $R_3$ is independently selected in each —O—CHR$_2$—CHR$_3$— unit;

$R_4$ is an alkylene group of about 2 to about 5 carbon atoms;

A is a polyamine moiety having at least one basic nitrogen atom;

x is an integer from about 1 to about 100; and y is an integer from about 1 to about 25.

2. The compound according to claim 1, wherein $R_1$ is a hydrocarbyl group having from about 1 to about 120 carbon atoms.

3. The compound according to claim 2, wherein $R_1$ is an alkyl group having about 1 to about 100 carbon atoms or an alkylphenyl group having an alkyl group containing about 1 to about 100 carbon atoms.

4. The compound according to claim 1, wherein at least one of $R_2$ and $R_3$ is hydrogen.

5. The compound according to claim 1, wherein $R_4$ is an alkylene group of about 4 to about 5 carbon atoms.

6. The compound according to claim 5, wherein $R_4$ is an alkylene group of about 5 carbon atoms.

7. The compound according to claim 1, wherein x is an integer of from about 1 to about 30.

8. The compound according to claim 7, wherein x is an integer of from about 1 to about 10.

9. The compound according to claim 1, wherein y is an integer of from about 1 to about 10.

10. The compound according to claim 1, wherein the polyamine moiety contains from about 2 to about 12 amine nitrogen atoms and from about 2 to about 40 carbon atoms.

11. The compound according to claim 10, wherein the polyamine moiety is derived from a polyalkylene polyamine containing from about 2 to about 12 amine nitrogen atoms and about 2 to about 24 carbon atoms.

12. The compound according to claim 11, wherein the polyalkylene polyamine has the formula:

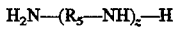

wherein $R_5$ is an alkylene group having about 2 to about 6 carbon atoms and z is an integer from about 1 to about 4.

13. The compound according to claim 12, wherein $R_5$ is an alkylene group having about 2 to about 4 carbon atoms.

14. The compound according to claim 13, wherein the polyalkylene polyamine is ethylene diamine or diethylene triamine.

15. The compound according to claim 14, wherein the polyalkylene polyamine is ethylene diamine.

16. A fuel composition comprising a major amount of hydrocarbons boiling in the gasoline or diesel fuel range and an effective deposit-controlling amount of a fuel-soluble compound of the formula:

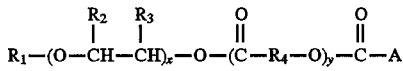

wherein $R_1$ is a hydrocarbyl group having a sufficient number of carbon atoms to render the compound soluble in hydrocarbons boiling in the gasoline or diesel fuel range;

$R_2$ and $R_3$ are each independently hydrogen or lower alkyl having about 1 to about 6 carbon atoms and each $R_2$ and $R_3$ is independently selected in each —O—$CHR_2$—$CHR_3$— unit;

$R_4$ is an alkylene group of about 2 to about 5 carbon atoms;

A is a polyamine moiety having at least one basic nitrogen atom;

x is an integer from about 1 to about 100; and y is an integer from about 1 to about 25.

17. The fuel composition according to claim 16, wherein $R_1$ is a hydrocarbyl group having from about 1 to about 120 carbon atoms.

18. The fuel composition according to claim 17, wherein $R_1$ is an alkyl group having about 1 to about 100 carbon atoms or an alkylphenyl group having an alkyl group containing about 1 to about 100 carbon atoms.

19. The fuel composition according to claim 16, wherein at least one of $R_2$ and $R_3$ is hydrogen.

20. The fuel composition according to claim 16, wherein $R_4$ is an alkylene group of about 4 to about 5 carbon atoms.

21. The fuel composition according to claim 20, wherein $R_4$ is an alkylene group of about 5 carbon atoms.

22. The fuel composition according to claim 16, wherein x is an integer of from about 1 to about 30.

23. The fuel composition according to claim 22, wherein x is an integer of from about 1 to about 10.

24. The fuel composition according to claim 16, wherein y is an integer of from about 1 to about 10.

25. The fuel composition according to claim 16, wherein the polyamine moiety contains from about 2 to about 12 amine nitrogen atoms and from about 2 to about 40 carbon atoms.

26. The fuel composition according to claim 25, wherein the polyamine moiety is derived from a polyalkylene polyamine containing from about 2 to about 12 amine nitrogen atoms and about 2 to about 24 carbon atoms.

27. The fuel composition according to claim 26, wherein the polyalkylene polyamine has the formula:

wherein $R_5$ is an alkylene group having about 2 to about 6 carbon atoms and z is an integer from about 1 to about 4.

28. The fuel composition according to claim 27, wherein $R_5$ is an alkylene group having about 2 to about 4 carbon atoms.

29. The fuel composition according to claim 28, wherein the polyalkylene polyamine is ethylene diamine or diethylene triamine.

30. The fuel composition according to claim 29, wherein the polyalkylene polyamine is ethylene diamine.

31. The fuel composition according to claim 16, wherein the composition contains about 50 to about 2,500 parts per million by weight of the fuel-soluble compound.

32. The fuel composition according to claim 16, wherein the composition further contains about 100 to about 5,000 parts per million by weight of a fuel-soluble, nonvolatile carrier fluid.

33. A fuel concentrate comprising an inert stable oleophilic organic solvent boiling in the range of from about 150° F. to about 400° F. and from about 10 to about 70 weight percent of a fuel-soluble compound of the formula:

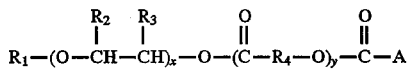

wherein $R_1$ is a hydrocarbyl group having a sufficient number of carbon atoms to render the compound soluble in hydrocarbons boiling in the gasoline or diesel fuel range;

$R_2$ and $R_3$ are each independently hydrogen or lower alkyl having about 1 to about 6 carbon atoms and each $R_2$ and $R_3$ is independently selected in each —O—$CHR_2$—$CHR_3$— unit;

$R_4$ is an alkylene group of about 2 to about 5 carbon atoms;

A is a polyamine moiety having at least one basic nitrogen atom;

X is an integer from about 1 to about 100; and y is an integer from about 1 to about 25.

34. The fuel concentrate according to claim 33, wherein $R_1$ is a hydrocarbyl group having from about 1 to about 120 carbon atoms.

35. The fuel concentrate according to claim 34, wherein $R_1$ is an alkyl group having about 1 to about 100 carbon atoms or an alkylphenyl group having an alkyl group containing about 1 to about 100 carbon atoms.

36. The fuel concentrate according to claim 33, wherein at least one of $R_2$ and $R_3$ is hydrogen.

37. The fuel concentrate according to claim 33, wherein $R_4$ is an alkylene group of about 4 to about 5 carbon atoms.

38. The fuel concentrate according to claim 37, wherein $R_4$ is an alkylene group of about 5 carbon atoms.

39. The fuel concentrate according to claim 33, wherein x is an integer of from about 1 to about 30.

40. The fuel concentrate according to claim 39, wherein x is an integer of from about 1 to about 10.

41. The fuel concentrate according to claim 33, wherein y is an integer of from about 1 to about 10.

42. The fuel concentrate according to claim 33, wherein the polyamine moiety contains from about 2 to about 12 amine nitrogen atoms and from about 2 to about 40 carbon atoms.

43. The fuel concentrate according to claim 42, wherein the polyamine moiety is derived from a polyalkylene polyamine containing from about 2 to about 12 amine nitrogen atoms and about 2 to about 24 carbon atoms.

44. The fuel concentrate according to claim 43, wherein the polyalkylene polyamine has the formula:

$$H_2N-(R_5-NH)_z-H$$

wherein $R_5$ is an alkylene group having about 2 to about 6 carbon atoms and z is an integer from about 1 to about 4.

45. The fuel concentrate according to claim 44, wherein $R_5$ is an alkylene group having about 2 to about 4 carbon atoms.

46. The fuel concentrate according to claim 45, wherein the polyalkylene polyamine is ethylene diamine or diethylene triamine.

47. The fuel concentrate according to claim 46, wherein the polyalkylene polyamine is ethylene diamine.

48. The fuel concentrate according to claim 33, wherein the fuel concentrate further contains about 20 to about 60 weight percent of a fuel-soluble, nonvolatile carrier fluid.

* * * * *